(12) United States Patent
Corma et al.

(10) Patent No.: US 7,358,401 B2
(45) Date of Patent: Apr. 15, 2008

(54) METHOD FOR MANUFACTURING CYCLOALKANOL AND/OR CYCLOALKANONE

(75) Inventors: Avelino Corma, Valencia (ES); Jose Manuel Lopez Nieto, Paterna (ES); Marcelo Eduardo Domine, Valencia (ES)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 11/390,314

(22) Filed: Mar. 28, 2006

(65) Prior Publication Data

US 2006/0224021 A1   Oct. 5, 2006

(30) Foreign Application Priority Data

Mar. 31, 2005   (JP) ............................ P2005-101690

(51) Int. Cl.
*C07C 45/27* (2006.01)
*C07C 35/08* (2006.01)

(52) U.S. Cl. ....................... 568/360; 568/836

(58) Field of Classification Search ...................... None
See application file for complete search history.

(56) References Cited

U.S. PATENT DOCUMENTS

| 4,859,798 A * | 8/1989 | Lyons et al. ................. 568/399 |
| 4,968,652 A | 11/1990 | Johnson et al. |
| 5,137,861 A | 8/1992 | Shih et al. |

FOREIGN PATENT DOCUMENTS

| EP | 0 222 597 A | 5/1987 |
| EP | 0 519 569 A2 | 12/1992 |
| EP | 1 074 537 A | 2/2001 |
| EP | 1 632 468 A | 3/2006 |
| JP | 10-505867 A | 6/1998 |
| JP | 11-509859 A | 8/1999 |
| JP | 2000-319211 A | 11/2000 |
| JP | 2003-261484 A | 9/2003 |
| WO | WO 92/11935 A | 7/1992 |
| WO | WO 97/08119 A1 | 3/1997 |
| WO | WO 99/40055 A1 | 8/1999 |

OTHER PUBLICATIONS

Nowotny et al. Increasing the Ketone Selectivity of the Cobalt-Catalyzed Radical Chain Oxidation of Cyclohexane. □□Chemistry—A European Journal, 2002, col. 8 (16), p. 3724-3731.*
Machmeyer et al. Designing a Solid Catalyst for the Selective Low-Temperature Oxidation of Cyclohexane to Cylohexanone. □□Angewandte Chemie, International Edition in English, 1997, vol. 36 (15), p. 1639-1642.*
Database WPI Section Ch, Week 198904 Derwent Publications XP-002397422 corresponds to JP 63-303936, published Dec. 12, 1988.
C. Nozaki et al., "Oxidation of Cyclohexane with Molecular Oxygen Efficiently Catalyzed by Di-Iron(III)-Substituted Silicotungstate, $\gamma$-SiW$_{10}${Fe(OH$_2$)}$_2$O$_{38}^{6-}$, Including Radical-chain Mechanism", Chemistry Letters 1998, pp. 1263-1264.

* cited by examiner

*Primary Examiner*—Sikarl A. Witherspoon
(74) *Attorney, Agent, or Firm*—Sughrue Mion, PLLC

(57) ABSTRACT

The object of the present invention is to provide a method for manufacturing cycloalkanol and/or cycloalkanone with favorable selectivity coefficient by oxidizing cycloalkane with favorable degree of conversion.

In the present invention, cycloalkane is oxidized with oxygen in the presence of a catalyst such that cobalt is supported on layer silicate cycloalkane. Said oxidation is performed in the coexistence of a heteropoly acid compound and the heteropoly acid compound preferably contains cobalt as a central element and/or a skeletal element.

10 Claims, 1 Drawing Sheet

METHOD FOR MANUFACTURING CYCLOALKANOL AND/OR CYCLOALKANONE

CROSS-REFERENCE TO RELATED APPLICATIONS

The present application claims priority under U.S.C. § 119 to Japanese Patent Application No. 2005-101690 (filed on Mar. 31, 2005, entitled "Method for Manufacturing Cycloalkanol and/or Cycloalkanone"). The contents of that application are incorporated herein by reference thereto in their entirety.

BACKGROUND OF THE INVENTION

1. Technical Field

The present invention relates to a method for manufacturing cycloalkanol and/or cycloalkanone by oxidizing cycloalkane with oxygen.

2. Description of the Related Art

The use of a cobalt catalyst is effective in manufacturing cycloalkanol and/or cycloalkanone by oxidizing cycloalkane with oxygen, and generally it has conventionally been known that the above-mentioned oxidation is performed in a homogeneous system by using a cobalt compound soluble in cycloalkane, such as cobalt carboxylate, for a catalyst. In addition, various heterogeneous catalyses have been proposed, for example, the above-mentioned oxidation by using a molecular sieve compound containing cobalt in a crystal lattice for a catalyst is disclosed in EP 0 519 569 A. Also, the above-mentioned oxidation by using a cobalt-containing compound prepared by a sol-gel method for a catalyst is disclosed in WO99/40055. Further, the above-mentioned oxidation by using a heteropoly acid compound containing cobalt as a skeletal element for a catalyst is disclosed in JP-A-2000-319211.

SUMMARY OF THE INVENTION

The above-mentioned conventional methods include unsatisfactory points in view of activity and selectivity of a catalyst, namely, degree of conversion of cycloalkane and selectivity coefficient of cycloalkanol and/or cycloalkanone. The object of the present invention is to provide a method of capably manufacturing cycloalkanol and/or cycloalkanone with favorable selectivity coefficient by oxidizing cycloalkane with favorable degree of conversion through oxidation of cycloalkane with the use of a cobalt catalyst, particularly a heterogeneous cobalt catalyst.

Through earnest studies, the inventors of the present invention have completed the present invention by finding out that the adoption of cobalt supported on layer silicate as a catalyst for oxidizing cycloalkane allows the above-mentioned object to be achieved. That is to say, the present invention provides a method for manufacturing cycloalkanol and/or cycloalkanone by oxidizing cycloalkane with oxygen in the presence of a catalyst such that cobalt is supported on layer silicate.

The present invention allows cycloalkanol and/or cycloalkanone to be manufactured with favorable selectivity coefficient by oxidizing cycloalkane with favorable degree of conversion.

DETAILED DESCRIPTION OF THE INVENTION

Figure 1:
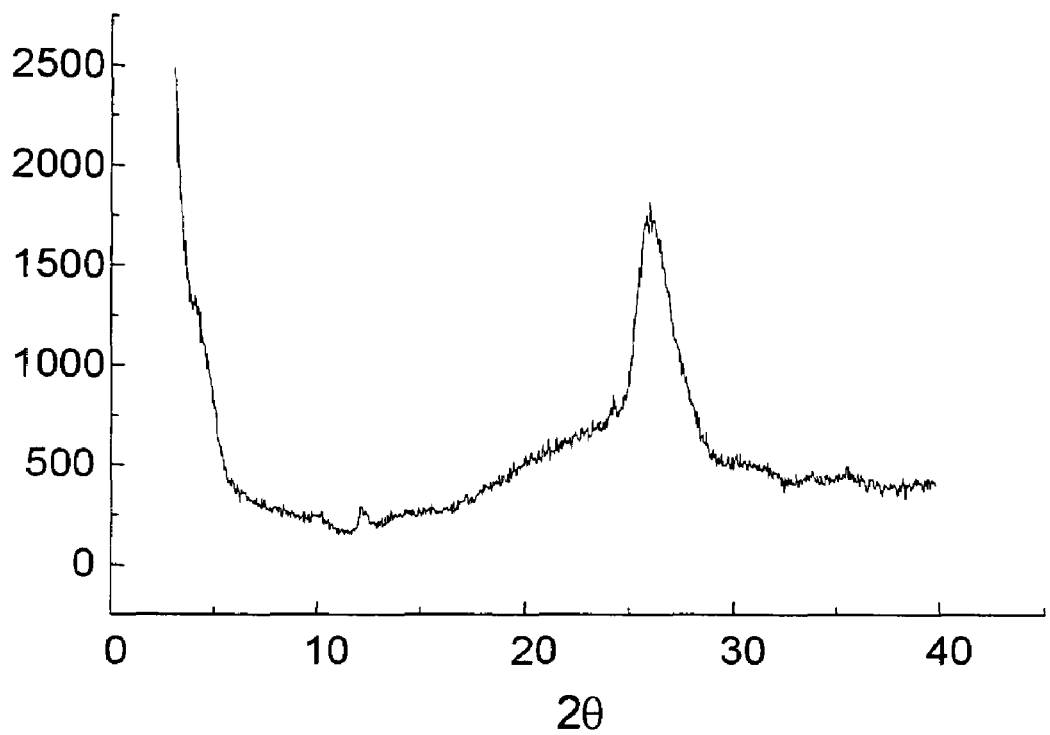
FIG. 1 is an X-ray diffraction pattern of cobalt-supporting kenyaite prepared according to the Reference Example 1 which had pillars formed at the interlayer thereof.

The present invention is hereinafter detailed. In the present invention, corresponding cycloalkanol and/or cycloalkanone are manufactured by using cycloalkane for raw materials to oxidize this with oxygen (molecular oxygen) in the presence of a catalyst.

Examples of cycloalkane for raw materials include, for example, monocyclic cycloalkane having no substituent in a ring such as cyclopropane, cyclobutane, cyclopentane, cyclohexane, cycloheptane, cyclooctane, cyclodecane and cyclooctadecane, polycyclic cycloalkane such as decalin and adamantane, and cycloalkane having substituent in a ring such as methylcyclopentane and methylcyclohexane, and also two kinds or more thereof can be used as required.

Oxygen-containing gas is typically used for oxygen source. This oxygen-containing gas may be, for example, air, pure oxygen, or air or pure oxygen diluted with inert gas such as nitrogen, argon and helium. Oxygen enriched air in which pure oxygen is added to air can also be used.

With regard to the present invention, cobalt supported on layer silicate (hereinafter occasionally referred to as 'cobalt-supporting layer silicate') is used as a catalyst for oxidizing cycloalkane with oxygen. The use of such a catalyst allows cycloalkanol and/or cycloalkanone to be manufactured with favorable selectivity coefficient by oxidizing cycloalkane with favorable degree of conversion.

Examples of layer silicate as a carrier include layer silicates derived from minerals such as makatite, kanemite, magadiite and kenyaite, and layer silicates such that a gap at the interlayer is widened by forming a columnar support (pillar) of silicate, silica and the like at its interlayer. Composite layer silicate such that a columnar support of silicate is formed at the interlayer can also be used, for example, MCM-36. In order to form pillars at the interlayer, it is preferable for layer silicate to be contacted with silicon compounds such as silicate ester, and then to be hydrolyzed.

The support percentage of cobalt is typically 0.01 to 20% in weight percentage with respect to a catalyst, namely, cobalt-supporting layer silicate, preferably 0.05 to 10% and more preferably 0.1 to 5%.

Examples of a method for supporting cobalt on layer silicate include, for example, a method such as to impregnate layer silicate with an aqueous solution of cobalt compounds such as halide of cobalt and carboxylate and oxo acid salt thereof, a method such as to immerse layer silicate in an aqueous solution of cobalt compounds and adsorb cobalt compounds and the like. Cobalt-supporting layer silicate can also be prepared by mixing cobalt compounds with silicon compounds and the like, which can be raw materials for layer silicate, to be subjected to hydrothermal synthesis reaction.

The oxidation reaction of cycloalkane can be performed by contacting cycloalkane with oxygen in the presence of cobalt-supporting layer silicate as a catalyst. The used quantity of a catalyst is typically 0.01 to 50 parts by weight with respect to 100 parts by weight of cycloalkane, preferably 0.1 to 10 parts by weight.

In order to improve degree of conversion of cycloalkane and selectivity coefficient of cycloalkanol and/or cycloalkanone, the use of a so-called co-catalyst is effective and kinds thereof are properly selected, among which the use of a heteropoly acid compound is advantageous. This heteropoly acid compound may be free heteropoly acid, or an acid salt or a normal salt of heteropoly acid. The structure of a heteropoly acid compound may be, for example, Keggin structure such that an atomic ratio of central element (hetero element)/skeletal element (poly element) is 1/12, Anderson structure such that the atomic ratio is 1/6 or Dawson structure such that the atomic ratio is 2/18.

Preferable examples of a heteropoly acid compound include a heteropoly acid compound containing cobalt as a central element and/or a skeletal element, preferably a heteropoly acid compound particularly containing cobalt as a central element and a skeletal element, specifically such that a heteropoly anion is $[CoW_{11}CoO_{39}]$ or $[CoMo_{11}CoO_{39}]$. Such a heteropoly acid compound can be prepared in conformance with a method described, for example, on p. 6025 of Vol. 112 in Journal of American Chemical Society, 1990.

A heteropoly acid compound may be molded for use or supported on a carrier, as required. This carrier is properly selected and a so-called hydrotalcite-like compound is preferably used. Here, a hydrotalcite-like compound is a layer compound, similar to hydrotalcite $[Mg_6Al_2(OH)_{16}(CO_3) \cdot 4H_2O]$, such that an anion exists between positively charged layers composed of bivalent metal and trivalent metal. In the case where a heteropoly acid compound is supported on a carrier, the support percentage thereof is typically 0.01 to 4% in weight percentage with respect to the total of a heteropoly acid compound and a carrier, preferably 0.1 to 2%.

In the case of using a heteropoly acid compound without being supported on a carrier, the quantity thereof is typically 0.001 to 10 parts by weight with respect to 100 parts by weight of cycloalkane, preferably 0.01 to 5 parts by weight. In the case of using a heteropoly acid compound supported on a carrier, the used quantity thereof is typically 0.01 to 50 parts by weight with respect to 100 parts by weight of cycloalkane in the total of a heteropoly acid compound and a carrier, preferably 0.1 to 10 parts by weight.

The reaction temperature is typically 0 to 200° C., preferably 50 to 170° C. and the reaction pressure is typically 0.01 to 10 MPa, preferably 0.1 to 2 MPa. The reaction solvent can be used as required, for example including nitrile solvents such as acetonitrile and benzonitrile, and carboxylic acid solvents such as acetic acid and propionic acid.

The after-treatment after oxidation reaction is not particularly limited, for example including a process such as to filter the reaction mixture to separate a catalyst therefrom, which mixture is thereafter washed by water and subsequently distilled. In the case where cycloalkylhydroperoxide corresponding to cycloalkane for raw materials is contained in the reaction mixture, cycloalkylhydroperoxide can be converted into intended cycloalkanol and cycloalkanone by alkali treatment and reduction treatment.

EXAMPLES

Examples of the present invention are hereinafter described and the present invention is not limited thereto. The analysis of cyclohexane, cyclohexanone, cyclohexanol and cyclohexyl hydroperoxide in reaction liquid was performed by gas chromatography, and degree of conversion of cyclohexane as well as each selectivity coefficient of cyclohexanone, cyclohexanol and cyclohexyl hydroperoxide were calculated from results of this analysis.

Reference Example 1

Preparation of a Cobalt-supporting Kenyaite Having Pillars Formed at its Interlayer (A) Preparation of a Cobalt-supporting Kenyaite To an aqueous solution of sodium hydroxide (0.13 g) in water (1.9 g) in a beaker, tyramine (1.17 g) and colloidal silica (LUDOX AS-40 manufactured by Aldrich, i.e., an aqueous suspension of 40 wt. % of silica) (2.5 g) were added, and the mixture was stirred. Then, an aqueous solution of cobalt (II) acetate tetrahydrate (0.14 g) in water (1.0 g) was added, and the mixture was stirred for 4 hours. This mixture was set in an autoclave and stirred at 150° C. for 10 days. After that, the mixture was filtered, and the resulting solid residue was washed with water and dried in an oven at 100° C. for a whole day and night. Thus, a cobalt-supporting kenyaite (1.1 g) was obtained.

(B) Formation of Pillars at the Interlayer of the Cobalt-supporting Kenyaite

Figure 2:
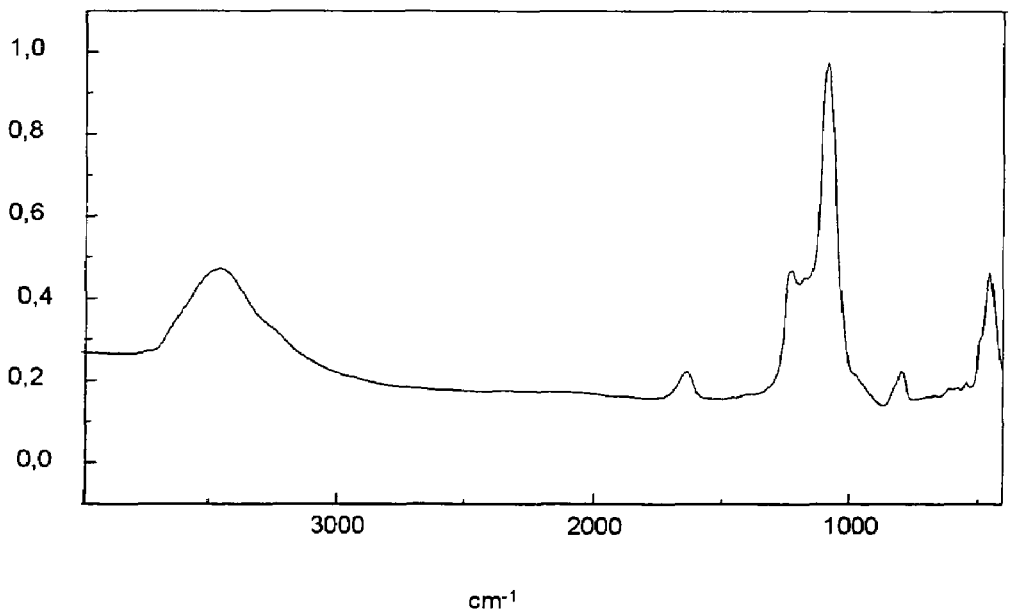
FIG. 2 is an infrared absorption spectrum of cobalt-supporting kenyaite prepared according to the Reference Example 1 which had pillars formed at the interlayer thereof.

The cobalt-supporting kenyaite (1.0 g) obtained in the above preparation (A), water (4.1 g), an aqueous solution (20.1 g) of 40 wt. % of cetyltrimethylammonium hydroxide, and an aqueous solution (6.1 g) of 30 wt. % of tetrapropylammnoium were charged in a flask, and the mixture was stirred and heated at 80° C. for 16 hours, and then was filtered. The resulting solid residue was washed with water and dried in an oven at 100° C. for a whole day and night. This solid was charged in a flask, and tetraethyl orthosilicate (5.0 g) was added thereto under a nitrogen atmosphere. The mixture was heated at 90° C. for 16 hours and was then filtered. The resulting solid residue was washed with ethanol and then washed with water, and dried in an oven at 100° C. for a whole day and night. This solid and water (100 g) were charged in a flask, and the mixture was stirred at room temperature for 7 hours and filtered. The resulting solid residue was washed with water and dried in an oven at 100° C. for a whole day and night. Then, the solid was baked at 540° C. for 7 hours to obtain a cobalt-supporting kenyaite which had pillars formed at the interlayer thereof. This cobalt-supporting kenyaite was subjected to an X-ray diffraction analysis (copper Kα-ray; see FIG. 1) and an elemental analysis. As a result, it was confirmed that the interlayer height was not lower than 37 Å; the cobalt content, 2.9 wt. %; the silicon content, 44.8 wt. %; and the sodium content, 0.04 wt. %. The cobalt-supporting kenyaite was further subjected to a Fourier transform infrared spectroscopic analysis. The result is shown in FIG. 2.

Reference Example 2

Preparation of a Hydrotalcite-like Compound Which Supports a Salt of Heteropoly Acid (a) Preparation of a Salt of Heteropoly Acid Sodium tungstate dihydrate (19.8 g, 0.06 mol) and water (40 g) were charged in a 500 ml round bottom flask, and stirred at room temperature to form an aqueous solution. To this aqueous solution, acetic acid (4.1 g) was added to adjust the pH thereof to 7. Then, the solution was heated under refluxing. To this solution, an aqueous solution of cobalt (II)

acetate tetrahydrate (2.5 g) in water (13 g) was added dropwise over 20 minutes, and the mixture was further heated under refluxing for 15 minutes. The mixture was cooled to a room temperature, and the solid precipitate was filtered off. Then, the resulting filtrate was heated under refluxing. To this filtrate, an aqueous solution of potassium chloride (13 g) in water (25 g) was added, and the mixture was further heated under refluxing for 15 minutes. The resulting mixture was cooled to a room temperature and then was left to stand at 5° C. for a whole day and night for crystallization. The resultant crystals (16.8 g) were separated by filtration, and were subjected to an elemental analysis, an X-ray diffraction analysis, an infrared spectrpscopic analysis and a UV-visible spectroscopic analysis. As a result, this crystal was found to be a potassium salt of a Keggin type heteropoly acid, i.e., $K_7H[Co^{II}W_{11}Co^{II}(H_2O)O_{39}] \cdot 14H_2O)$, which contained cobalt as the core element, and tungsten and cobalt as the skeletal elements.

(b) Purification of the Salt of Heteropoly Acid

To an aqueous solution (10 ml) of acetic acid (0.05 g) in water, the crystals of the salt of heteropoly acid (3.0 g) obtained in the above preparation (a) were added, and the mixture was heated to 100° C., and then, the insoluble substances were filtered off. The resulting filtrate was cooled to a room temperature, and was admixed with a saturated aqueous solution (10 ml) of potassium chloride and left to stand at 5° C. for a whole day and night for crystallization. The resulting crystals (1.68 g) were separated by filtration. The crystals were subjected to an elemental analysis, an X-ray diffraction analysis, an infrared spectroscopic analysis and a UV-visible spectroscopic analysis. As a result, this crystal was found to be a potassium salt of a Keggin type heteropoly acid, i.e., $K_7H[Co^{II}W_{11}Co^{II}(H_2O)O_{39}]14H_2O$, which contained cobalt as the core element, and tungsten and cobalt as the skeletal elements. Thus, it was confirmed that the composition and structure of the salt of heteropoly acid obtained in the above preparation (a) were maintained.

(c) Preparation of a Hydrotalcite-like Compound

Sodium nitrate (18.9 g), sodium hydroxide (10.6 g) and water (82 g) were charged in a 500 ml round bottom flask, and the mixture was stirred at room temperature to form an aqueous solution. To this aqueous solution, an aqueous solution of zinc nitrate tetrahydrate (32.7 g) and aluminum nitrate (15.6 g) in water (63 g) was added dropwise at a rate of 60 ml/hour. Then, water was distilled off from this mixture at 60° C. over 18 hours. After that, the resulting solid was separated by filtration, and was repeatedly washed with water until the pH of the water used for the washing reached 7. After the washing, the solid was dried at 60° C. for a whole day and night to obtain a solid (16.5 g), which was found to be a hydrotalcite-like compound as the result of the X-ray diffraction analysis.

(d) Supporting of the Salt of Heteropoly Acid on the Hydrotalcite-like Compound

Under a nitrogen atmosphere, the crystals (2.0 g) of the salt of heteropoly acid, obtained by repeating the above purification (b) several times, were added to and dissolved in water (74 g) by heating at 60° C. Under a nitrogen atmosphere, to this solution, the hydrotalcite-like compound (3.9 g) obtained in the above preparation (c) was added, and the mixture was stirred at 60° C. for 22 hours. The solid was separated from this mixture by filtration, and was washed with water (27.1 g) of 60° C. and dried to obtain a solid (3.8 g). The solid obtained was subjected to an elemental analysis, an X-ray diffraction analysis, an infrared spectroscopic analysis and a UV-visible spectroscopic analysis. As a result, it was confirmed that the above salt of heteropoly acid was supported on the above hydrotalcite-like compound in this solid.

Example 1

34 g (0.40 mol) of cyclohexane and 0.2 g of the above-mentioned cobalt-supporting kenyaite were put in a 50-ml autoclave, and the inside of the system was pressurized up to 0.5 MPa with oxygen at room temperature and thereafter heated up to a temperature of 130° C. and reacted under the flow of oxygen for 24 hours.

At a point in time of 5.5 hours after the start of the reaction, degree of conversion of cyclohexane was 3.5%, selectivity coefficient of cyclohexanone was 44.3%, selectivity coefficient of cyclohexanol was 52.1% and selectivity coefficient of cyclohexyl hydroperoxide was 0.1%. At a point (the end) in time of 24 hours after the start of the reaction, degree of conversion of cyclohexane was 5.4%, selectivity coefficient of cyclohexanone was 63.7%, selectivity coefficient of cyclohexanol was 24.3% and selectivity coefficient of cyclohexyl hydroperoxide was 0.2%.

Example 2

34 g (0.40 mol) of cyclohexane, 0.1 g of the cobalt-supporting kenyaite obtained according to the Reference Example 1 which had pillars formed at the interlayer thereof and 0.1 g of the above-mentioned heteropoly acid salt-supporting hydrotalcite-like compound obtained according to the Reference Example 2 were put in a 50-ml autoclave, and the inside of the system was pressurized up to 0.5 MPa with oxygen at room temperature and thereafter heated up to a temperature of 130° C. and reacted under the flow of oxygen for 24 hours.

At a point in time of 6 hours after the start of the reaction, degree of conversion of cyclohexane was 5.5%, selectivity coefficient of cyclohexanone was 52.0%, selectivity coefficient of cyclohexanol was 40.7% and selectivity coefficient of cyclohexyl hydroperoxide was 1.3%. At a point (the end) in time of 24 hours after the start of the reaction, degree of conversion of cyclohexane was 9.8%, selectivity coefficient of cyclohexanone was 67.2%, selectivity coefficient of cyclohexanol was 18.1% and selectivity coefficient of cyclohexyl hydroperoxide was 0.4%.

Comparative Example 1

34 g (0.40 mol) of cyclohexane and 0.2 g of the above-mentioned heteropoly acid salt-supporting hydrotalcite-like compound obtained according to the Reference Example 2 were put in a 50-ml autoclave, and the inside of the system was pressurized up to 0.5 MPa with oxygen at room temperature and thereafter heated up to a temperature of 130° C. and reacted under the flow of oxygen for 24 hours.

At a point in time of 6 hours after the start of the reaction, degree of conversion of cyclohexane was 0.2%, selectivity coefficient of cyclohexanone was 25.6%, selectivity coefficient of cyclohexanol was 21.8% and selectivity coefficient of cyclohexyl hydroperoxide was 52.6%. At a point (the end) in time of 24 hours after the start of the reaction, degree of conversion of cyclohexane was 5.4%, selectivity coefficient of cyclohexanone was 58.6%, selectivity coefficient of cyclohexanol was 32.9% and selectivity coefficient of cyclohexyl hydroperoxide was 0.2%.

The major embodiments and the preferred embodiments of the present invention are listed below.

[1] A method for manufacturing cycloalkanol and/or cycloalkanone wherein cycloalkane is oxidized with oxygen in the presence of a catalyst such that cobalt is supported on layer silicate.

[2] The method according to [1], wherein the layer silicate is selected from the group consisting of makatite, kanemite, magadiite and kenyaite.

[3] The method according to [1], wherein the layer silicate is kenyaite.

[4] The method according to any one of [1] to [3], wherein the layer silicate has pillars formed at the interlayer thereof.

[5] The method according to any one of [1] to [4], wherein said oxidation is performed in the coexistence of a heteropoly acid compound.

[6] The method according to [5], wherein the heteropoly acid compound contains cobalt as a central element and/or a skeletal element.

[7] The method according to any one of [5] and [6], wherein the heteropoly acid compound is supported on a carrier.

[8] The method according to [7], wherein the carrier is a hydrotalcite-like compound.

[9] The method according to any one of [1] to [8], wherein the cycloalkane is cyclohexane.

What is claimed is:

1. A method for manufacturing cycloalkanol and/or cycloalkanone comprising the oxidation of cycloalkane with oxygen in the presence of a catalyst such that cobalt is supported on layer silicate, wherein the layer silicate has pillars formed at the interlayer thereof.

2. The method according to claim 1, wherein the layer silicate is selected from the group consisting of makatite, kanemite, magadiite and kenyaite.

3. The method according to claim 1, wherein the layer silicate is kenyaite.

4. The method according to any one of claims 1 to 3, wherein said oxidation is performed in the presence of a heteropoly acid compound.

5. The method according to claim 4, wherein the heteropoly acid compound contains cobalt as a central element and/or a skeletal element.

6. The method according to claim 4, wherein the heteropoly acid compound is supported on a carrier.

7. The method according to claim 6, wherein the carrier is a hydrotalcite-like compound.

8. The method according to any one of claims 1 to 3, wherein the cycloalkane is cyclohexane.

9. The method according to claim 1, wherein said oxidation is performed in the presence of a heteropoly acid compound.

10. The method according to claim 8, wherein said oxidation is performed in the presence of a heteropoly acid compound.

* * * * *